United States Patent [19]

Bello

[11] Patent Number: 5,919,227
[45] Date of Patent: Jul. 6, 1999

[54] MOVING ARTIFICIAL EYE

[76] Inventor: Louis Bello, 248 Manassas Dr., Manassas Pk, Va. 20111

[21] Appl. No.: 08/927,589

[22] Filed: Sep. 11, 1997

[51] Int. Cl.[6] .......................................................... A61F 2/14
[52] U.S. Cl. ............................... 623/4; 446/341; 446/342; 446/343; 446/345; 446/389; 446/392
[58] Field of Search ................ 623/4; 446/341, 446/342, 343, 345, 389, 392

[56] References Cited

U.S. PATENT DOCUMENTS

| | | | |
|---|---|---|---|
| 1,268,885 | 6/1918 | Sampson | 623/4 |
| 2,295,890 | 9/1942 | Conrad | 446/392 |
| 3,120,720 | 2/1964 | Brudney | 623/4 |
| 4,637,159 | 1/1987 | Kulis | 446/389 |
| 4,828,531 | 5/1989 | Kuhn | 446/389 X |
| 4,875,888 | 10/1989 | Harvey | 446/392 |

FOREIGN PATENT DOCUMENTS 614850  6/1961  Italy ........................................ 446/392

*Primary Examiner*—David J. Isabella
*Assistant Examiner*—Choon P. Koh

[57] ABSTRACT

An artificial eye that appears to look back at a plurality of observers simultaneously even while either change position.

3 Claims, 1 Drawing Sheet

MOVING ARTIFICIAL EYE

FIELD OF INVENTION

This invention relates generally to reproductions of eyes of the sort that appear to move so as to look back at a plurality of observers simultaneously.

BACKGROUND OF THE INVENTION

DESCRIPTION OF PRIOR ART

Very realistic glass and plastic eyes abound. Mechanically moveable eyes have long been in existence. Eyes that appear to move on their own are unique. This is the field to which my invention relates.

SUMMARY OF THE INVENTION

The invention is an artificial eye comprising an imitation outer eyelid supporting a clear eyeball with a white rear shell which will serve as a background. Said eyeball contains, centrally, a colored, transparent ball within which, also centrally located, there is a dark ball. The assembly resembles an eye. An observer sees the dark ball (pupil) always centrally located within the colored, transparent ball (iris) within the eyeball which in turn is surrounded by the white background. This condition is maintained automatically as the observer changes position. The eyelids enhance the illusion. To the observer, the white background of the shell at the rear of the eyeball appears to be the white of a real eye, thus completing the effect.

In actual practice plastics may be used, the eyeball, iris, and pupil may be flattened at the rear to save material, the eyeball may be hollow, the parts may be differently colored for special effects, the iris can be enhanced by the introduction of other matter during the semi liquid molding stage of manufacture in order to better imitate real eyes, the eyelids may be omitted if an opening already exists, and the white background shell may support the iris when the eyeball is optionally omitted. Alternately, the white background may support a two dimensional rendition of an iris and pupil.

BRIEF DESCRIPTION OF THE DRAWINGS

For a better comprehension of the invention, reference will be had to the accompanying page of drawings (Page 1 of 1) in which.

DESCRIPTION OF THE PREFERRED EMBODIMENTS

Figure 1:
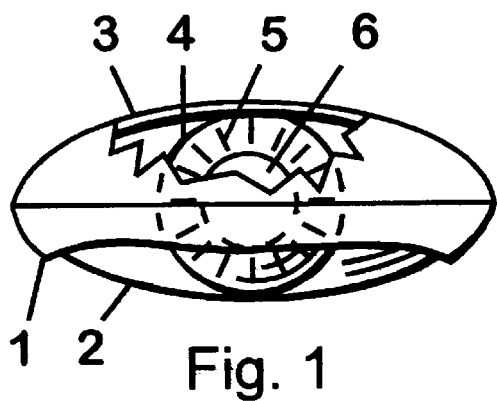
FIG. 1 is a top view perspective with cutaway showing the eyelids (1), the eyeball (2), a white, background shell (3), and centrally containing within a colored, transparent ball (iris 4) which itself contains "spokes" (5) radiating from its center and centrally containing a dark ball (pupil 6).
Figure 2:
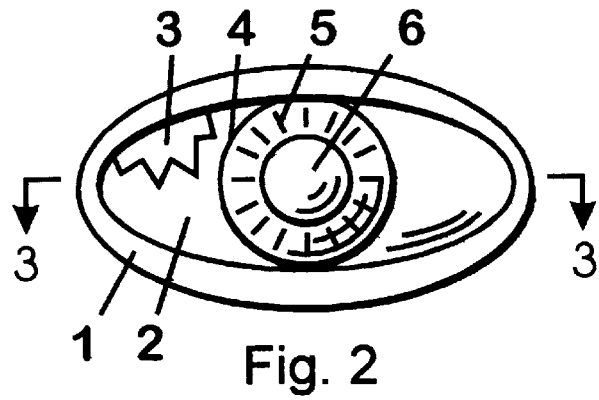
FIG. 2 is a front perspective view of the eye in which the same parts are shown, namely: The eyelids (1), the eyeball (2), the white, background shell (3), and centrally containing within a colored, transparent ball (iris 4) which itself contains "spokes" (5) radiating from its center and centrally containing within the iris (4) a dark ball (pupil 6).

Referring to the figure page's FIGS. 1 and 2, there is shown the device, containing the eyelids (1), the eyeball (2), the white, background shell (3), and centrally containing within a colored, transparent ball (iris 4) which itself contains "spokes" (5) radiating from it's center and centrally containing within said iris (4) a dark ball (pupil 6).

Figure 3:
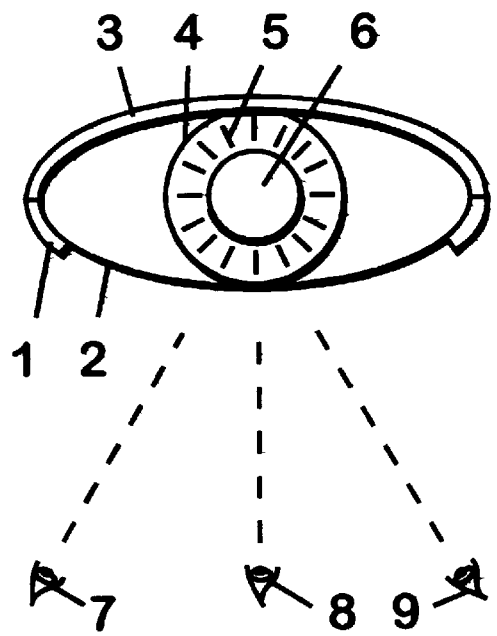
FIG. 3 is a cross-sectional top view of FIG. 2 taken along line 3—3, and showing the same parts in relation to three differently positioned observers numbered respectively, 7, 8, and 9.

FIG. 3 shows the same parts with the addition of three observers in order to illustrate the resulting effect. To observer 7, the black ball (6) appears as the eye's pupil (6), centered within the iris (4), with it's centrally radiating "spokes" (5) which are made of lines of darker pigment captive within the material since manufacture*. The eyelid's (1) left corner appears closer to the iris (4), and the right side corner of the eyelid (1) appears farther, creating the illusion that the eye is looking at the observer. To observer 8, all parts of the eye appear centered, and he also believes the eye is looking at him. To observer 9, the black ball (6) appears as the eye's pupil, centered within the iris (4), with it's centrally radiating "spokes" (5) which are made of lines of darker pigment captive within the material since manufacture*. The eyelid's (1) right corner appears closer to the iris (4), and the left side corner of the eyelid (1) appears farther, creating the illusion that the eye is looking at him also. Should any of these observers, or the eye, change position, the eye will seem to follow them.

Note: Centrally radiating spokes of color or other material is effected during the liquid shaping of the ball. The introduction of foreign matter into plastic or glass during manufacture is a very old art form.

Figure 4:
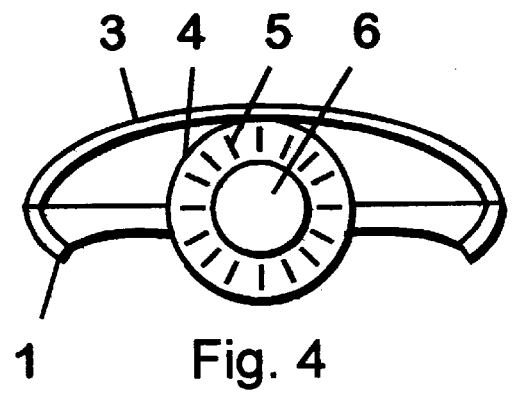
FIG. 4 is a cross-sectional top view of the device in which the transparent eyeball (2) has been omitted, and only the eyelids (1), white, background shell (3), and the colored, transparent ball (iris 4) containing "spokes" (5) radiating from it's center and centrally containing a dark ball (pupil 6) remain.
Figure 5:
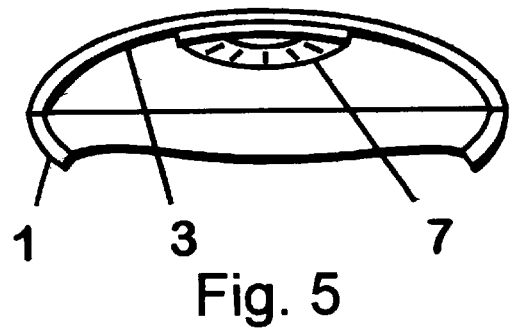
FIG. 5 is a cross-sectional view of the device showing the eyelids (1), the white background shell (3), and a two dimensional rendition of an iris and pupil (7).

FIG. 4 shows, cross-sectionally looking down, an embodiment excluding the eyeball (2). Another model (FIG. 5) replaces the iris (4), and pupil (6), with a two dimensional rendition of those parts (7). The eyeball (2), has been omitted for clarity, but may be used in this model.

I claim:

1. An artificial eye comprising an limitation outer eyelid, on its rear edge supporting a shell, an eyeball within the shell and eyelid assembly, said eyeball centrally containing a colored, transparent ball (iris) within which, also centrally located, there is a ball, (pupil), causing an observer to believe the eye is continually looking at him even as either moves.

2. An artificial eye comprising an outer shell at the rear and an eyeball attached, centrally containing a colored, transparent ball (iris) within which, also centrally located there is a ball (pupil) causing an observer to believe that the eye is continually looking at him even as either moves.

3. An artificial eye comprising an outer eyelid supporting an outer shell at the rear, centrally containing a colored, transparent ball (iris) within which, also centrally located, there is a ball (pupil), allowing an observer to believe that the eye is continually looking at him even as either moves.

* * * * *